US007482441B2

(12) United States Patent
Osterrieder et al.

(10) Patent No.: US 7,482,441 B2
(45) Date of Patent: Jan. 27, 2009

(54) ARTIFICIAL CHROMOSOMES COMPRISING EHV SEQUENCES

(75) Inventors: Nikolaus Osterrieder, Wampen (DE); Jens Rudolph, Insel Riems (DE)

(73) Assignee: Boehringer Ingelheim Vetmedica GmbH, Ingelheim (DE)

( * ) Notice: Subject to any disclaimer, the term of this patent is extended or adjusted under 35 U.S.C. 154(b) by 250 days.

(21) Appl. No.: 10/772,806

(22) Filed: Feb. 5, 2004

(65) Prior Publication Data

US 2006/0160202 A1 Jul. 20, 2006

Related U.S. Application Data

(63) Continuation of application No. 10/105,828, filed on Mar. 25, 2002, now abandoned.

(60) Provisional application No. 60/289,203, filed on May 7, 2001.

(30) Foreign Application Priority Data

Apr. 3, 2001 (DE) ................................ 101 16 594

(51) Int. Cl.
| | |
|---|---|
| *C07H 21/04* | (2006.01) |
| *C12N 15/64* | (2006.01) |
| *C12N 15/00* | (2006.01) |
| *C12N 15/74* | (2006.01) |
| *A61K 39/12* | (2006.01) |
| *A61K 39/245* | (2006.01) |
| *A61K 39/116* | (2006.01) |
| *A61K 39/00* | (2006.01) |
| *A61K 39/275* | (2006.01) |

(52) U.S. Cl. ..................... 536/23.1; 435/91.4; 435/440; 435/475; 424/229.1; 424/199.1; 424/202.1; 424/203.1

(58) Field of Classification Search ....................... None
See application file for complete search history.

(56) References Cited

U.S. PATENT DOCUMENTS

| | | | |
|---|---|---|---|
| 5,084,271 | A | 1/1992 | Studdert |
| 6,193,983 | B1 | 2/2001 | Crabb et al. |
| 6,277,621 | B1 | 8/2001 | Horsburg et al. |

OTHER PUBLICATIONS

Neubauer et al., Equine Herpesvirus 1 Mutants Devoid of Glycoprotein B or M are Apathogenic for Mice but Induce Protection against Challenge Infection 1997, Virology, vol. 239 No. 1, pp. 36-45.*
McGregor et al., Recent Advances in Herpesvirus Genetics Using Bacterial Artificial Chromosomes 2001, Molecular Genetics and Metabolism, vol. 72 No. 1, pp. 8-14.*
D. Schumacher et al: "Reconstitution of Marek's Disease Virus Serotype 1 (MDV-1) from DNA Cloned as a Bacterial Artificial Chromosome and Characterization of a Glycoprotein B-Negative MDV-1 Mutant" Journal of Virology, the American Society for Microbiology, US, vol. 74, No. 23, Dec. 2000, pp. 11088-11098.
M. Messerle et al: "Cloning and mutagenesis of a herpesvirus genome as an infectious bacterial artificial chromosome" Proceedings of the National Academy of Sciences of USA, National Academy of Science. Washington, US, vol. 94, No. 26, Dec. 1, 1997, pp. 14759-14763.
J. Rudolph et al: "Cloning of theGenomes of Equine Herpesvirus Type 1 (EHV-1) Strains KyA and RacL11 as Bacterial Artificial Chromosomes (BAC)." Journal of Veterinary Medicine Series B, vol. 49, No. 1, Feb. 2002, pp. 31-36.
J. Rudolph and N. Osterrieder: "Equine herpesvirustype 1 devoid of gM and gp2 is severelyimpaired in virus Egress but Not Direct Cell-to-Cell Spread." Virology, vol. 293, No. 2, Feb. 15, 2002, pp. 356-367.
W. Brune et al: "Forward with BACs—new tools for herpesvirus genomics" Trends in Genetics, Elsevier, Amsterdam, NL, vol. 16, No. 6, Jun. 2000, pp. 254-259.
Alistair McGregor et al: "Recent Advances in Herpesvirus Genetics Using Bacterial Artificial Chromosomes." Molecular Genetics and Metabolism, vol. 72, No. 1, Jan. 2001, pp. 8-14.
Granoff A, Webster R G (eds): "Encyclopedia of Virology" 1999, Academic Press, Harcourt Brace, San Diego, CA, USA XP001121578; O'Callaghan, D. J., and Osterrieder, N.: "Equine Herpesvirus (hERPESVIRIDAE)" p. 508- p. 515.
E.A.R. Telford et al: "The DNA Sequence of Equine Herpesvirus-4" The Journal of General Virology, England May 1998, vol. 79 (pt5), May 1998, pp. 1197-1203.
D. R. Fitzpatrick and M. J. Studdert: Immunologic Relationships Between Equine Herpesvirus Type 1 (Equine Abortion Virus) and type 4 (Equine Rhinoneumonitis Virus): American Journal of Veterinary Research, vol. 45, No. 10, Oct. 1, 1984, pp. 1947-1952.
P.H. Huebert et al: "Alternations in the equine herpesvirus type-1 (EHV-1) strain RacH during attenuation." Zentralblatt Fur Veterinarmedizin. Reihe B. Journal of Veterinary Medicine. Series B, Germany Mar. 1996, vol. 43, No. 1, pp. 1-14.
Neubauer et al. "Equine herpesvirus 1 mutants devoid of glycoprotein B or M are apathogenic for mice but induce protection agains challenge infection." Virology, 1997: 239: 36-45.
T. Matsumura et al: "Lack of virulence of the murine fibroblast adapted strain, Kentucky a (KyA), of equine herpesvirus type 1 (EHV-1) in young horses" Veterinary Microbiology, Amsterdam, NL, vol. 48, No. 3-4, 1996, pp. 353-365.
A. Neubauer et al: "Analysis of the Contributions of the Equine Herpesvirus 1 Glycoprotein gB Homolog to Virus Entry and Direct Cell-to-Cell Spread." Virology. United States Jan. 20, 1997, vol. 227, No. 2, pp. 281-294.

(Continued)

*Primary Examiner*—Bruce Campell
*Assistant Examiner*—Benjamin P Blumel
(74) *Attorney, Agent, or Firm*—Michael P. Morris; Mary-Ellen M. Devlin

(57) ABSTRACT

The invention belongs to the field of animal health, in particular equine diseases caused by equine herpesvirus (EHV). The invention relates to artificial chromosomes comprising the genome of equine herpesviruses, methods of producing attenuated or virulent EHV with or without the insertion of foreign genes, EHV obtainable with said methods and pharmaceutical compositions comprising said viruses.

9 Claims, 7 Drawing Sheets

OTHER PUBLICATIONS

Figure 1:
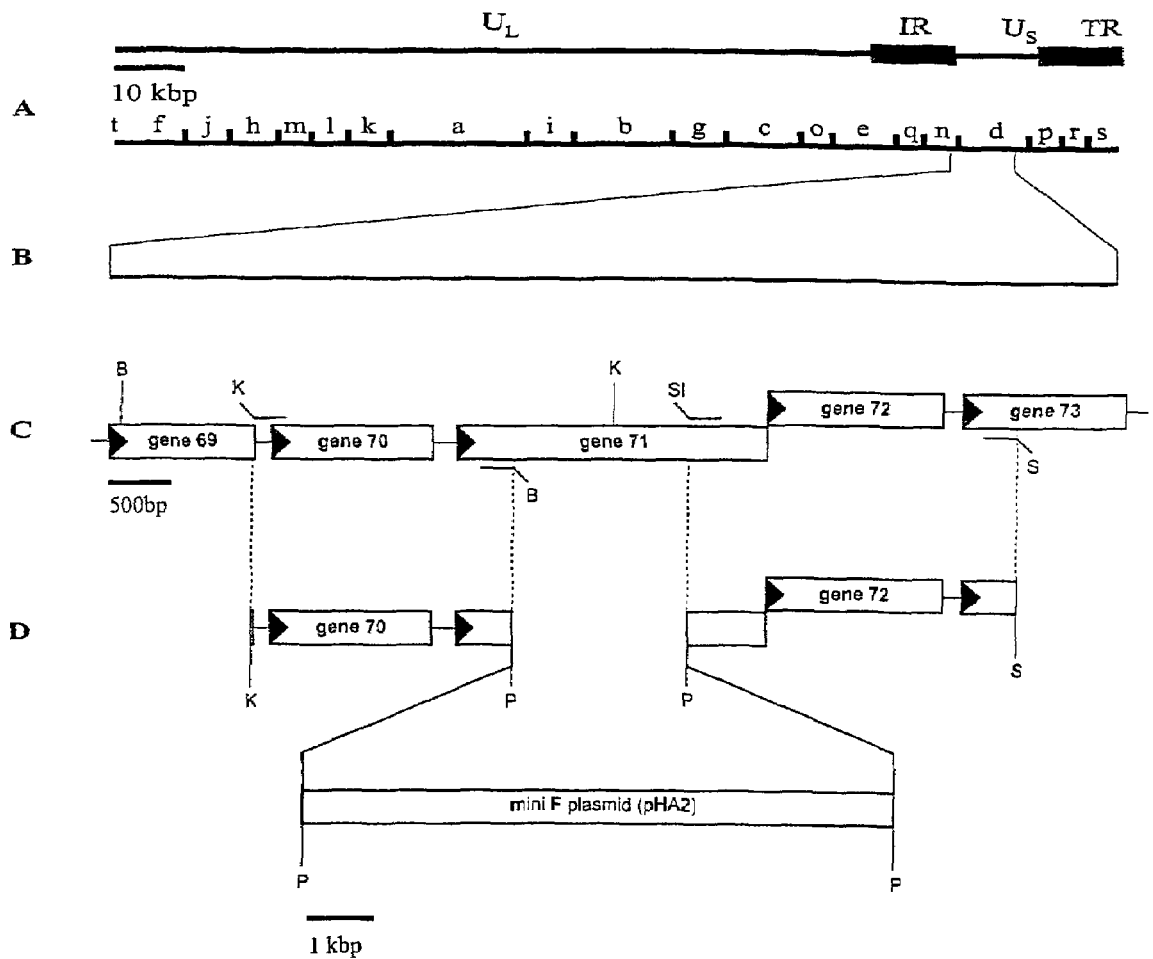

A. Neubauer et al: "Die Mutationen Im US2-und Glykoprotein B-Gen des Equinen Herpesvirus 1-Impfstammes RacH haben keinen Einfluss auf seine Attenuierung" "Mutations within the US2 and Glycoprotein B genes of the Equine Herpesvirus 1 Vaccine Strain Rach Do not Account for Its Attenuation" Berliner und Muenchener Tieraerztliche Wochenschrift, Paul Parey, Berlin, De, vol. 112, No. 9, Sep. 1999, pp. 351-354.

N. Osterrieder: "Construction and characterization of an equine herpesvirus 1 glycoprotein C negative mutant." Virus Research, Netherlands, Feb. 1999, vol. 59, No. 2, pp. 165-177.

H. Csellner et al: "EHV-1 glycoprotein D (EHV-1gD) is required for virus entry and cell-cell fusion, and an EHV-1 gD deletion mutant induces a protective immune respponse in mice." Archives of Virology, vol. 145, No. 11, 2000, pp. 2371-2385.

T. Matsumura et al: "An Equine Herpesvirus Type 1 Recombinant with a Deletion in the gE and gI Genes is Avirulent in Young Horses." Virology. United States Mar. 1, 1998, vol. 242, No. 1, Mar. 1, 1998, pp. 68-79.

H. E. Farrell et al: "Vaccine Potential of a Herpes Simplex Virus Type 1 Mutant with an Essential Glycoprotein Deleted" Journal of Virology, the American Society for Microbiology, US, vol. 68, No. 2, Feb. 1, 1994, pp. 927-932.

L. Hutchinson et al: "Herpes Simplex Virus Glycoprotein K Promotes Egress of VirusParticles." Journal of Virology. United States Sep. 1995, vol. 69, No. 9, Sep. 1995, pp. 5401-5413.

"Recombinant Herpesviruses Lacking Gene for Glycoprotein L" Research Disclosure; Keneth Mason Publications, Emsworth, GB, No. 371, Mar. 1, 1995, pp. 129-130.

A. Neubauer et al: "Equine Herpesvirus 1 Mutants Devoid of Glycoprotein B or M are Apathogenic for Mice by Induce Protection against Challenge Infection" Virology, Academic Press, Orlando, US, vol. 239, No. 1, Dec. 8, 1997, pp. 36-45.

N. Osterrieder et al: "Deletion of genE 52 encoding glycoprotein M or equine herpesvirus type 1 strain RacH results in increased immunogenicity." Veterinary Microbiology, vol. 81, No. 3, Aug. 8, 2001, pp. 219-226.

K. R. Marshall et al: "An Equine Herpesvirus-1 Gene 71 Deletant is Attenuated and Elicits a Protective Immune Response in Mice." Virology, Academic Press, Orlando, US, vol. 231, No. 1, 1997, pp. 20-27.

Yi Sun et al: "The role of the gene 71 product in the life cycle of equine herpesvirus 1" Journal of General Virology, Society for General Microbiology, Reading, GB, vol. 77, No. 3, Mar. 1, 1996 pp. 493-500.

M. Suter et al: "BAC-VAC, a novel generation of (DNA) vaccines: A bacterial artificial chromosome (BAC) containing a replication-competant, packaging-defective virus genome induces protective immunity against herpes simplex virus 1." Proceedings of the National Academy of Sciences of USA, National Academy of Science, Washington, US, vol. 98, No. 22, Oct. 26, 1999, pp. 12697-12702.

E. A. R. Telford et al: "The DNA Sequence of Equine Herpesvirus-1." Virology, Academic Press, Orlando, US, vol. 189, No. 1, 1992, pp. 304-316.

A. Mayr et al: "Untersuchungen zur Entwicklung eines Lebendimpfstoffes gegen die Rhinopneumonitis (Stutenabort) der Pferde" Journal of Veterinary Medicine, Series B-Zentralblatt Fuer Veterinaermedizin, Reine B. Paul Parey, Berlin, DE, vol. 15, 1968, pp. 406-418.

Translation of A. Mayr et al. "Investigations towards the Development of a Live Vaccine against Equine Rhinopneumonitis-1" 1968, pp. 406-418.

O'Callaghan, et al; Equine Herpesvirus (Herpesviridae); Encyclopedia of Virology; vol. 8; pp. 508-515; published 1999; Academic Press; XP-001121578.

Fraefel, et al; Immediate-Early Transcription over Covalently Joined Genome Ends of Bovine Herpesvirus 1: the circ Gene; Journal of Virology; vol. 67, No. 3; pp. 1328-1333; Mar. 1993; American Society of Microbiology; XP009053697.

Chowdhury, et al; Genomic Termini of Equine Herpesvirus 1; Journal of Virology; vol. 64, No. 2; pp. 873-880; Feb. 1990; American Society for Microbiology; XP009053696.

Garber, et al; Demonstration of Circularization of Herpes Simplex Virus DNA Following Infection Using Pulsed Field Gel Electrophoresis; Virology; vol. 197; pp. 459-462; 1993; Academic Press.

Gray; Regulation of Equine Herpesvirus Type 1 Gene Expression: Characterization of Immediate Early, Early, and Late Transcription; Virology; vol. 158; pp. 79-87; 1987; Academic Press.

* cited by examiner

| Agarose gel | Southern blot |
| HindIII digest | (kan^R probe) |

ARTIFICIAL CHROMOSOMES COMPRISING EHV SEQUENCES

The invention belongs to the field of animal health, in particular equine diseases caused by equine herpesvirus (EHV). The invention relates to artificial chromosomes comprising the genome of equine herpesviruses, methods of producing attenuated EHV viruses, EHV viruses obtainable with said methods and pharmaceutical compositions comprising said viruses.

BACKGROUND OF THE INVENTION

Equine herpesvirus 1 (EHV-1), a member of the Alphaherpesvirinae, is the major cause of virus-induced abortion in equids and causes respiratory and neurological disease. The entire DNA sequence of the EHV-1 strain Ab4p has been determined (Telford, E. A. R. et al., 1992). Only few genes and gene products have been characterized for their relevance for the virulence or immunogenicity of EHV-1 because the production of viral mutants is still relying on the generation of recombinant viruses by homologous recombination between the viral genome and respective foreign DNA to be inserted in cultured mammalian cells.

For control of EHV-1 infections, two different approaches are followed. First, modified live vaccines (MLVs) have been developed, including the strain RacH (Mayr, A. et al., 1968; Hübert, P. H. et al., 1996), which is widely used in Europe and the United States. Second, inactivated vaccines and independently expressed viral glycoproteins have been assessed for their immunogenic and protective potential. Among the glycoproteins that were expressed using recombinant baculoviruses are the glycoproteins (g) B, C, D, and H, which induced partial protection against subsequent challenge EHV-1 infection in a murine model (Awan, A. R. et al:, 1990; Tewari, D. et al., 1994; Osterrieder, N. et al., 1995; Stokes, A. et al., 1996). However, the use of MLVs has advantages over killed and subunit vaccines. MLVs are highly efficient in inducing cell-mediated immune responses, which are most likely to be responsible for protection against disease (Allen, G. P. et al., 1995; Mumford, J. A. et al., 1995).

Herpesvirus glycoproteins are crucially involved in the early stages of infection, in the release of virions from cells, and in the direct cell-to-cell spread of virions by fusion of neighboring cells. To date, 11 herpes simplex virus type 1 (HSV-1)-encoded glycoproteins have been identified and have been designated gB, gC, gD, gE, gG, gH, gI, gJ, gK, gL, and gM. HSV-1 mutants lacking gC, gE, gG, gI, gJ, and gM are viable, indicating that these genes are dispensable for replication in cultured cells. Comparison of the HSV-1 and equine herpesvirus 1 nucleotide sequences revealed that all of the known HSV-1 glycoproteins are conserved in EHV-1. According to the current nomenclature, these glycoproteins are designated by the names of their HSV-1 homologs. In addition, a further envelope protein named gp1/2 and a tegument protein, the VP13/14 homolog of HSV-1, have been described to be glycosylated in case of EHV-1 (reviewed in Osterrieder et al., 1998). It is known that EHV-1 gC, gE gI, and gM are not essential for growth in cell culture, whereas gB and gD appear to be essential for virus growth in cultured cells. The contributions of other EHV-1 glycoproteins to replication in cultured cells are not known (Neubauer et al., 1997; Flowers et al., 1992).

The gp1/2 glycoprotein is encoded by gene 71 (Wellington et al., 1996; Telford et al., 1992) and was also shown to be nonessential for virus growth in vitro (Sun et al., 1996). In addition, a viral mutant carrying a lacZ insertion in the gene 71 open reading frame was apathogenic in a murine model of infection but still able to prevent against subsequent challenge infection (Sun et al., 1996; Marahall et al. 1997). In addition, the KyA strain of EHV-1 harbors a major deletion in the coding sequences of gene 71 (Colle et al., 1996).

The technical problem underlying this invention was to provide a new tool and procedure to generate attenuated equine herpesviruses of defined specificity.

SUMMARY OF THE INVENTION

The above-captioned technical problem is solved by the embodiments characterized in the claims and the description.

The invention relates to artificial chromosomes comprising the genome of EHV, methods of producing attenuated EHV, EHV obtainable with said methods and pharmaceutical compositions comprising said viruses.

FIGURE LEGENDS

FIG. 1:

Cloning strategy for introduction of mini F plasmid sequences into the RacH genome (A). PCR amplification of fragments bordering gene 71 located in the US region of the genome (B) was done and the resulting BamHI-KpnI and SalI-SphI fragments were consecutively cloned into vector pTZ18R(C). Mini F plasmid sequences were released from recombinant plasmid pHA2 (Adler et al., 2000) with PacI and cloned to give rise to recombinant plasmid p71-pHA2 (D). This plasmid was co-transfected with RacH DNA into RK13 cells and fluorescing virus progeny was selected. Viral DNA from green fluorescing virus progeny was used to transform *Escherichia coli* DH10B cells from which infectious RacH-BAC was isolated. Restriction enzyme sites and scales (in kbp) are given.

FIG. 2:

Restriction enzyme digests of RacH and RacH-BAC. After separation by 0.8% agarose gel electrophoresis, fragments were transferred to a nylon membrane (Pharmacia-Amersham) and hybridized with a labelled pHA2 probe (see FIG. 1). Reactive fragments which are present due to insertion of mini F plasmid sequences are indicated by asterisks. Molecular weight marker is the 1 kb ladder (Gibco-BRL). The restriction enzymes used are indicated.

FIG. 3:

Plaque sizes of RacH and RacH-BAC. Plaque sizes were determined on RK13 cells by measuring diameters of 150 plaques each. Plaque sizes of RacH were set to 100%, respectively, and plaque sizes of virus progeny reconstituted from BAC were compared to those of the parental virus. Standard deviations are given.

FIG. 4:

Principle of the deletion of the genes encoding for gD (a) or gM (b) in RacH-BAC by replacing the open reading frames with the kanamycin resistance gene ($kan^R$) using E/T cloning. The $kan^R$ gene was amplified by PCR using the primers listed in Table 1, and the amplicon was electroporated into DH10B cells containing RacH-BAC and plasmid pGETrec which expresses the enzymes necessary for E/T cloning after arabinose induction (Schumacher et al., 2000). Kanamycin-resistant colonies were picked, DNA was isolated and subjected to Southern blot analysis using a $kan^R$-specific probe. In both gD-negative RacH-BAC (c) and gM-negative RacH-BAC (d), fragments of the expected sizes (gD: 20.4 kbp; gM: 9.3 kbp specifically reacted with the $kan^R$ probe.

DETAILED DESCRIPTION OF THE INVENTION

Before the embodiments of the present invention it must be noted that as used herein and in the appended claims, the singular forms "a", "an", and "the" include plural reference unless the context clearly dictates otherwise. Thus, for example, reference to "a virus" includes a plurality of such viruses, reference to the "cell" is a reference to one or more cells and equivalents thereof known to those skilled in the art, and so forth. Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies which are reported in the publications which might be used in connection with the invention. Nothing herein is to be construed as an admission that the invention is not entitled to antedate such disclosure by virtue of prior invention.

The invention relates to an artificial chromosome vector characterized in that it comprises essentially the entire genome of an EHV strain from which infectious progeny can be reconstituted after transfection into a permissive cell.

With the artificial chromosome vectors according to the present invention, safe EHV-vaccines comprising EHV with defined attenuations can be generated. Such viruses are useful for the preparation of a safe live vaccine for use in the prevention and/or treatment of EHV infections (see infra). The invention provides the possibility for a fast and efficient manipulation of the EHV genome which remains fully infectious for eukaryotic cells or is modified into a replication-deficient virus. There was a long lasting need in the art for such a tool to handle and manipulate the huge genome of EHV. Lastly, the EHV nucleic acid can be used as a polynucleotide vaccine which is applied either topically or systemically to naive or primed horses and may also be applied in utero.

The present invention is illustrated in example 1 showing the cloning of the entire genome of EHV-1 as an infectious mini F plasmid ('bacterial artificial chromosome', BAC) into *Escherichia coli*. The generation of said BAC was not trivial and was posed many difficulties, including the preparation and extraction of sufficient amounts of circular DNA. The circularized form of recombinant viral DNA was needed to transform DH10B cells with the recombinant DNA in order to prepare the mini F plasmid-cloned EHV DNA. To obtain sufficient amounts of circular viral DNA, early viral transcription was blocked by the addition of 100 μg per ml of cycloheximide after infection of cells. Viral DNA was then prepared and used for transformation of DH10B cells. Only from cells treated with cycloheximide was it possible to extract sufficient amounts of circular DNA and to obtain DH10B clones containing the entire RacH genome.

"Essentially" means that the EHV genome is complete with the exception that it may carry a mutation as set out infra.

"Artificial chromosome" relates to any known artificial chromosomes, such as yeast, or preferably bacterial artificial chromosomes.

Preferably, a bacterial artificial chromosome (BAC) according to the invention is a vector used to clone large DNA fragments (100- to 300-kb insert size) in *Escherichia coli* cells which is based on naturally occurring F-factor plasmid found in the bacterium *E. coli* (Shizuya, H., B. Birren, U. J. Kim et al. 1992. Cloning and stable maintenance of 300-kilobase-pair fragments of human DNA in *Escherichia coli* using an F-factor-based vector. Proceedings National Academy of Science 89: 8794-8797). The type of vector is preferably based on a F-plasmid replicon containing the origin of replication (oriS) and its own DNA polymerase (repE) as well as the genes parA and parB involved in maintaining its copy number at a level of one or two per *E. coli*. The antibiotic resistance marker is preferably Cm-resistance.

The invention preferably relates to an artificial chromosome vector according to the invention, characterized in that the EHV is EHV-1.

The invention preferably relates to an artificial chromosome vector according to the invention, characterized in that the EHV is EHV-4.

The invention preferably relates to an artificial chromosome vector according to the invention, characterized in that the EHV strain is RacH.

According the invention, any type of mutation can be introduced into the EHV genome, in order to obtain a replication-deficient and/or attenuated EHV virus. Such mutations include, but are not limited to any mutation (e.g. deletion, insertion, substitution) relating to the glycoproteins gB, gC, gD, gE, gG, gI, gJ, gL and gM, gp1/2 and any combination thereof. Preferably, said mutations are deletion mutations, i.e. the respective glycoproteins such as e.g. gM are completely deleted.

Thus, the invention preferably relates to an artificial chromosome vector according to the invention, characterized in that the EHV strain is lacking the glycoprotein gB.

The invention preferably relates to an artificial chromosome vector according to the invention, characterized in that the EHV strain is lacking the glycoprotein gC.

The invention preferably relates to an artificial chromosome vector according to the invention, characterized in that the EHV strain is lacking the glycoprotein gD.

The invention preferably relates to an artificial chromosome vector according to the invention, characterized in that the EHV strain is lacking the glycoprotein gE.

The invention preferably relates to an artificial chromosome vector according to the invention, characterized in that the EHV strain is lacking the glycoprotein gG.

The invention preferably relates to an artificial chromosome vector according to the invention, characterized in that the EHV strain is lacking the glycoprotein gH.

The invention preferably relates to an artificial chromosome vector according to the invention, characterized in that the EHV strain is lacking the glycoprotein gI.

The invention preferably relates to an artificial chromosome vector according to the invention, characterized in that the EHV strain is lacking the glycoprotein gK.

The invention preferably relates to an artificial chromosome vector according to the invention, characterized in that the EHV strain is lacking the glycoprotein gL.

The invention preferably relates to an artificial chromosome vector according to the invention, characterized in that the EHV strain is lacking the glycoprotein gM.

The invention preferably relates to an artificial chromosome vector according to the invention, characterized in that the EHV strain is lacking the glycoprotein gp1/2.

The invention preferably relates to an artificial chromosome vector according to the invention, characterized in that the artificial chromosome is a bacterial artificial chromosome (BAC). Said BAC's can be propagated in any bacterium known to the skilled person, e.g. and preferably *Escherichia coli*.

The invention preferably relates to an artificial chromosome vector according to the invention, characterized in that the artificial chromosome is a yeast artificial chromosome (YAC).

The invention preferably relates to an artificial chromosome vector RacH-BAC according to the invention, characterized in that the artificial chromosome as deposited under the accession number ECACC 01032704 with the ECACC in Porton Down, UK (European Collection of Cell Cultures, CAMR, Salisbury, Wiltshire SP4 0JG, UK), on Mar. 27, 2001, by Dr. N. Osterrieder (Bodden Blick 5A, Insel Riems, D-17498 Germany). The viability of this deposit was tested and confirmed on Mar. 27, 2001, and is capable of reproduction.

Another important embodiment of the present invention is a polynucleotide vaccine encoding an an artificial chromosome vector or EHV contained therein according to the invention.

Yet another important embodiment of the present invention is the use of an artificial chromosome vector according to the invention for the generation of infectious EHV.

The invention furthermore relates to a method for the generation of an infectious EHV, characterized in that an artificial chromosome vector according to the invention is used to infect a suitable cell line and the shedded virus is collected and purified.

The invention furthermore relates to a method for the generation of an attenuated EHV, characterized in that the EHV sequence contained in an artificial chromosome vector according to the invention is specifically modified by molecular biology techniques.

Said modifications may be carried out by methods known in the art, e.g. site directed mutagenesis see e.g. Sambrook et al. (1989) Molecular Cloning: A Laboratory Manual, $2^{nd}$ ed., Cold Spring Harbor Laboratory Press, Cold Spring Harbor, N.Y.

Furthermore, the invention relates to a EHV obtainable by a method according to the invention.

Another very important embodiment is a pharmaceutical composition comprising a polynucleotide according to the invention and optionally pharmaceutically acceptable carriers and/or excipients. Such a polynucleotide according to the invention may also be used in a pharmaceutical composition within the scope of this invention, e.g. for DNA vaccination.

One example of a targeted system of administration, e.g. for polynucleotides according to the invention is a colloidal dispersion system. Colloidal dispersion systems comprise macromolecule complexes, nanocapsules, microspheres and lipid-based systems including oil-in-water emulsions, micelles, mixed micelles and liposomes or liposome formulations. Liposomes are the preferred colloidal system according to the invention. Liposomes are artificial membrane vesicles which are useful as carriers in vitro and in vivo. These formulations may carry a cationic, anionic or neutral charge. It has been shown that large unilamellar vesicles (LUV) ranging from 0.2-4.0 μm in size may enclose a major part of an aqueous buffer solution with large macromolecules. RNA, DNA and intact virions can be encapsulated in the aqueous phase inside and transported to the target in a biologically active form (Fraley R et al., 1981, Trends Biochem Sci 6, 77-80). In addition to mammalian cells, liposomes have also proved suitable for the targeted transporting of nucleotides into plant, yeast and bacterial cells. In order to be an efficient gene transfer carrier the following properties should be present: (1) the genes should be enclosed with high efficiency without reducing their biological activity; (2) there should be preferential and substantial binding to the target cell compared with non-target cells; (3) the aqueous phase of the vehicle should be transferred highly efficiently into the target cell cytoplasm; and (4) the genetic information should be expressed accurately and efficiently (Mannino R. J. et al., 1988, BioTechniques 6, 682-690).

The composition of the liposomes usually consists of a combination of phospholipids, particularly high phase transition temperature phospholipids, e.g. combined with steroids such as cholesterol. Other phospholipids or other lipids may also be used. The physical characteristics of the liposomes depend on the pH, the ion concentration and the presence of divalent cations.

The pharmaceutical composition according to the invention may also contain a vector according to the invention, e.g. a BAC vector comprising an EHV genome as described supra, as a naked "gene expression vector". This means that the vector according to the invention is not associated with an adjuvant for targeted administration (e.g. liposomes, colloidal particles, etc.). A major advantage of naked DNA vectors is the absence of any immune response caused by the vector itself.

The EHV nucleic acid can be used as a polynucleotide vaccine (see pharmaceutical composition, supra) which is applied either topically (e.g. intranasally) or systemically to naive or primed horses and may also be applied in utero.

Another very important embodiment is a pharmaceutical composition comprising an EHV virus according to the invention and pharmaceutically acceptable carriers and/or excipients. A pharmaceutically acceptable carrier can contain physiologically acceptable compounds that act, for example, to stabilize or to increase the absorption or form part of a slow release formulation of the EHV virus or the polynucleotide according to the invention. Such physiologically acceptable compounds include, for example, carbohydrates, such as glucose, sucrose or dextrans, antioxidants, such as ascorbic acid or glutathione, chelating agents, low molecular weight proteins or other stabilizers or excipients (see also e.g. Remington's Pharmaceutical Sciences (1990). 18th ed. Mack Publ., Easton). One skilled in the art would know that the choice of a pharmaceutically acceptable carrier, including a physiologically acceptable compound, depends, for example, on the route of administration of the composition.

Furthermore, the invention relates to the use of a polynucleotide according to the invention in the manufacture of a vaccine for the prevention and/or treatment of EHV infections.

Furthermore, the invention relates to the use of an EHV virus according to the invention in the manufacture of a vaccine for the prevention and/or treatment of EHV infections.

Furthermore, the invention relates to the use of the BAC technology to establish a highly virulent and genetically well characterized EHV which can be used for immunization and challenge studies for use e.g. in vaccine potency studies.

Furthermore, the invention relates to the use of EHV BACs according to the invention to generate mutant BACs that are generated taking into account appearing genetic or antigenetic variants of EHV. This relates to one or more mutations present withing, new variants' of EHV which can be easily introduced in the existing EHV BAC.

The following example is intended to aid the understanding of the invention and should in no way be regarded as limiting the scope of the invention.

EXAMPLE 1

Construction of an EHV-1 Bacterial Artificial Chromosome

A genetically uniform population of RacH ($256^{th}$ passage) was isolated. With RacH, passage 257, Rk13 cells were infected and a mother pool was established. Virus of one additional passage on RK13 cells was used to infect RK13 cells, from which viral DNA was prepared. Ten micrograms (μg) of viral DNA were co-transfected with 10 μg of plasmid p71-pHA2 (FIG. 1) into RK13 cells. For construction of plasmid p71-pHA2, 2.0 and 2.4 kbp fragments on either side of the EHV-1 gene 71 (FIG. 1; Table 1) were amplified by polymerase chain reaction (PCR) using primers containing appropriate restriction enzyme sites (Table 1). Both fragments were subsequently cloned into pTZ18R (Pharmacia-Amersham) to obtain plasmid p71 (FIG. 1). A BAC vector (pHA2; Messerle et al., 1997) containing the Eco-gpt and GFP (green flourescent protein) genes under the control of the HCMV (human cytomegalovirus) immediate early promoter was released as a PacI fragment from plasmid pHA2 and inserted into the PacI sites of the 2.0 and 2.4 kbp fragment cloned in p71 (FIG. 1; Table 1). Virus progeny was harvested and individual plaques expressing the green fluorescent protein (GFP) were isolated and subjected to three rounds of plaque purification until virus progeny stained homogenously green under the fluorescent microscope (Seyboldt et al., 2000). Similarly, co-transfections of p71-pHA2 and DNA of EHV-1 strain Kentucky A (KyA) were performed and the recombinant virus was purified to homogeneity. Recombinant virus DNA was prepared (Schumacher et al., 2000) and electroporated into Escherichia coli strain DH10B (Messerle et al., 1997; Schumacher et al., 2000). Electrocompetent bacteria were prepared as described (Muyrers et al., 1999; Narayanan et al., 1999; Zhang et al., 1998) and electroporation was performed in 0.1 cm cuvettes at 1250 V, a resistance of 200 Ω, and a capacitance of 25 μF (Easyject electroporation system, Eurogenentec). Transformed bacteria were incubated in 1 ml of Luria-Bertani (LB) medium (28) supplemented with 0.4% glucose for 1 hr at 37° C., and then plated on LB agar containing 30 μg/ml chloramphenicol. Single colonies were picked into liquid LB medium, and small scale preparations of BAC DNA were performed by alkaline lysis of Escherichia coli (Schumacher et al., 2000). Large scale preparation of BAC DNA was achieved by silica-based affinity chromatography using commercially available kits (Qiagen, Macherey & Nagel).

Figure 2:
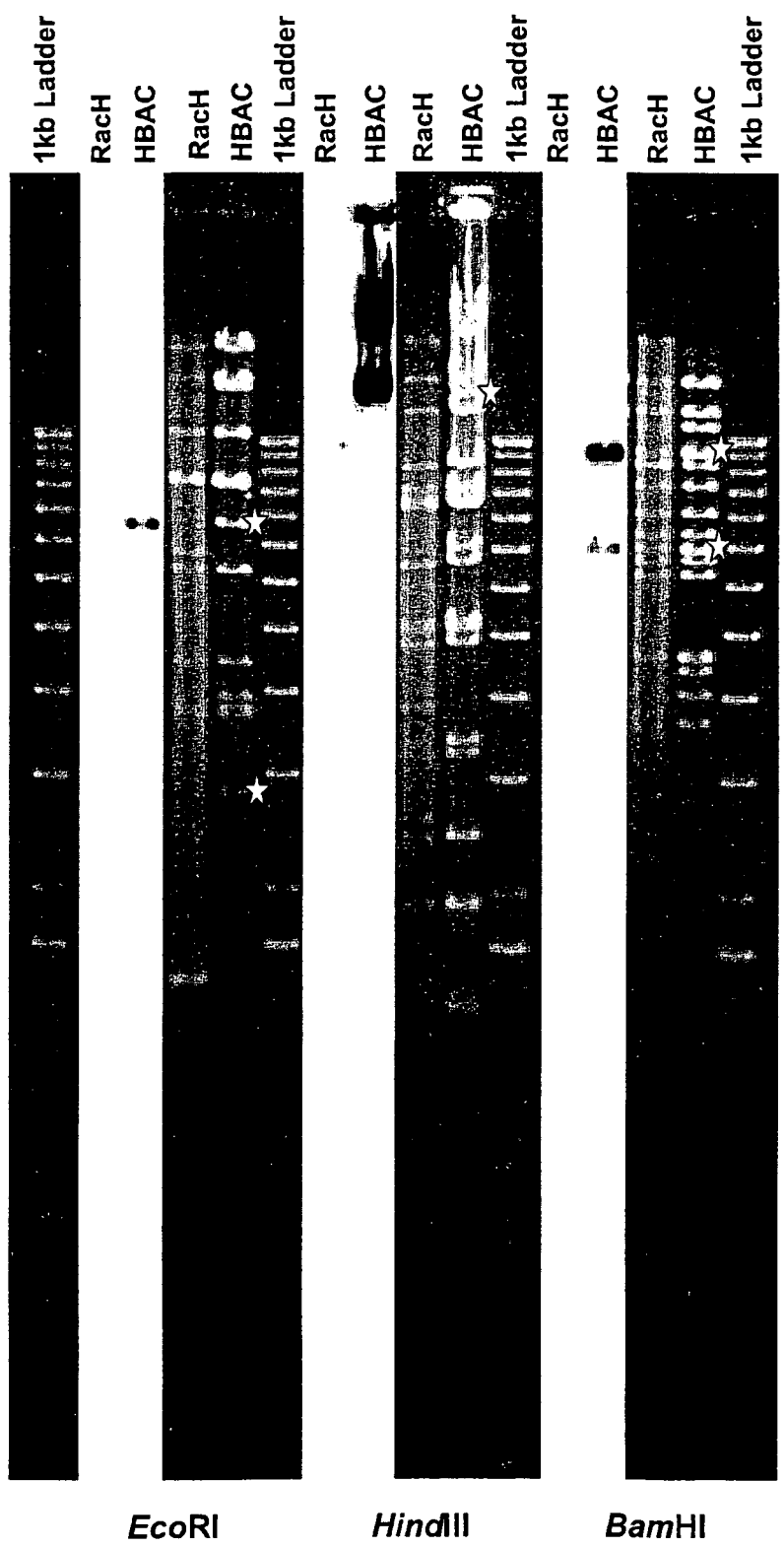
Figure 3:
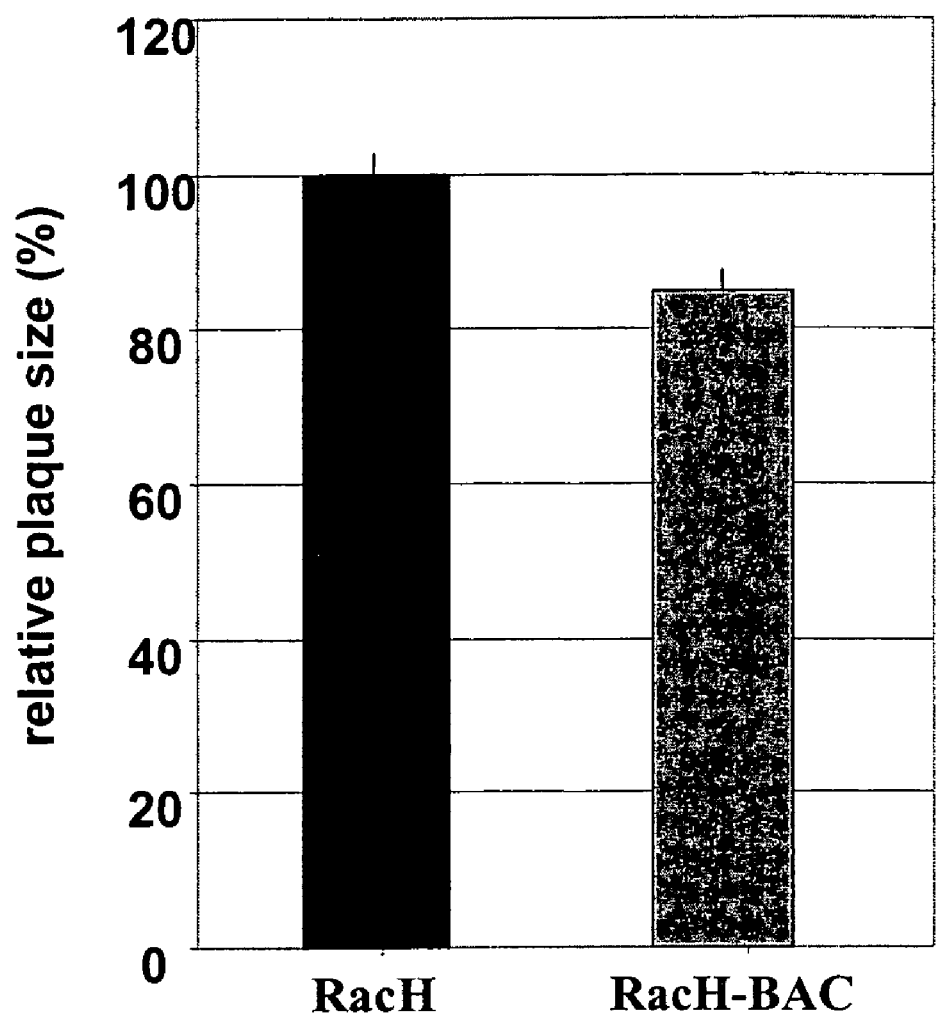
Figure 4A:
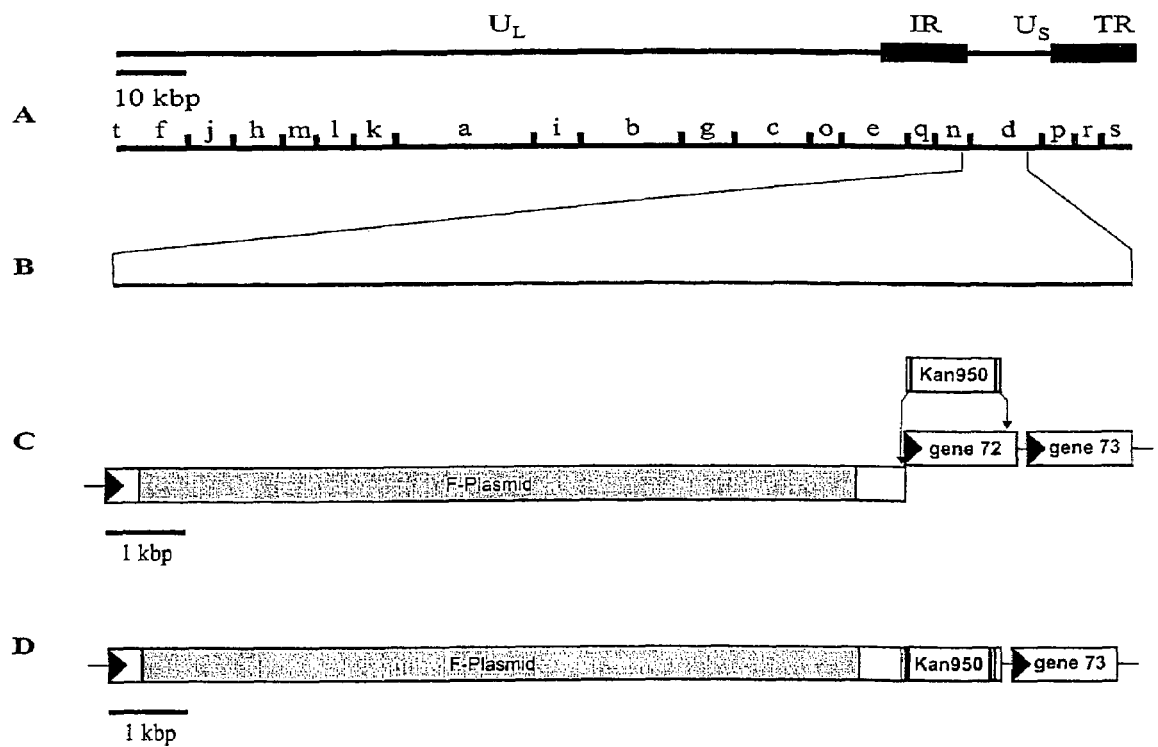
Figure 4B:
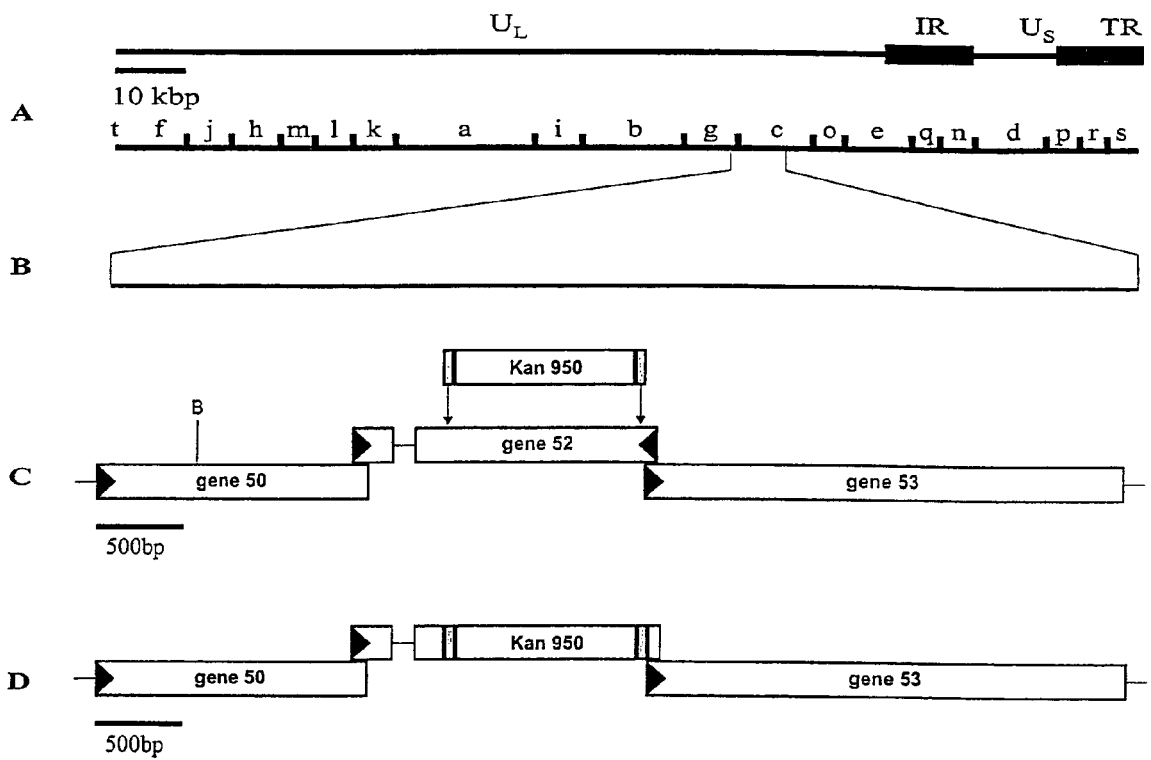
Figure 4C:
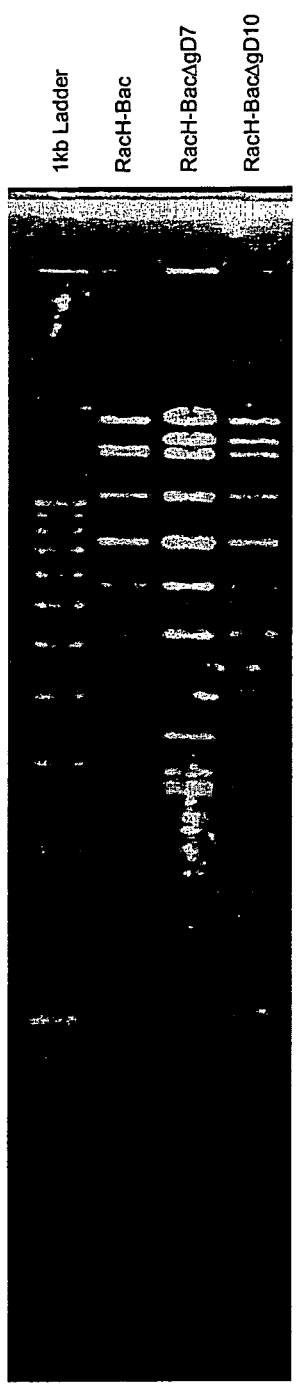
Figure 4C:
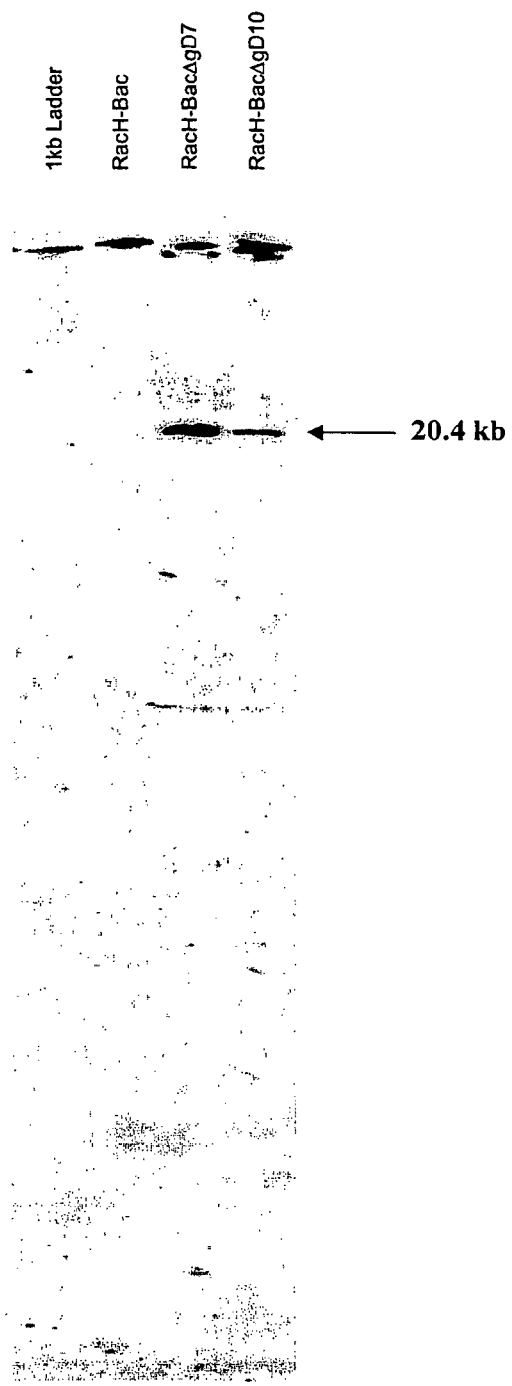
Figure 4D:
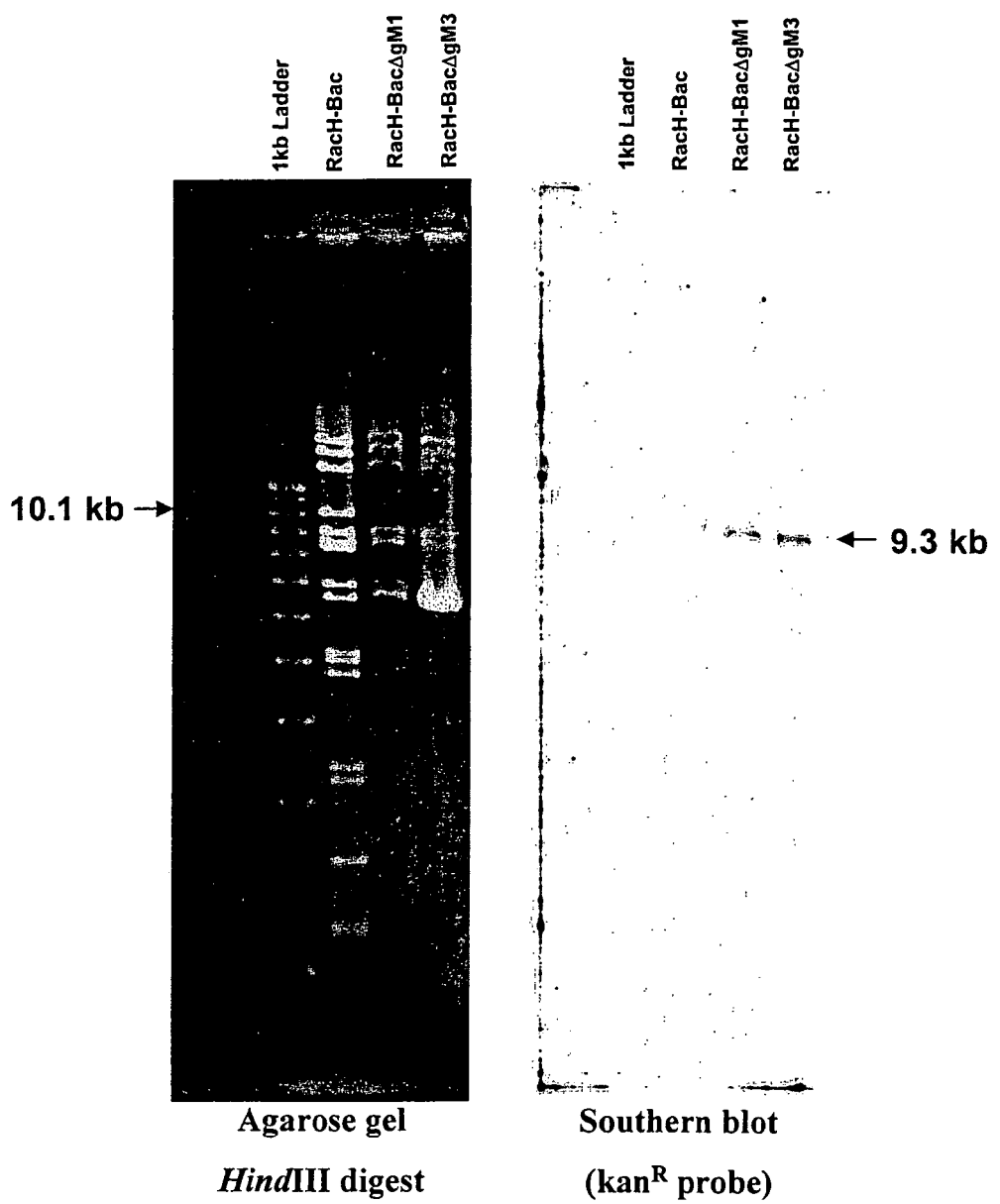

From the chloramphenicol-resistant bacterial colonies, one colony each was chosen and named RacH-BAC which contained the EHV-1 RacH genome. RACH-BAC DNA was cleaved with restriction enzymes BamHI, EcoRI and HindIII and the restriction enzyme patterns were compared to those of parental viral DNA. (Schumacher et al., 2000). The calculated and expected changes in the banding pattern after insertion of the mini F plasmid into the gene 71 locus were observed in RacH-BAC. In contrast, no other differences in restriction enzyme patterns as compared to the parental virus were obvious (FIG. 2). After purification of RacH-BAC DNA using affinity chromatography, RK13 cells were transfected with 1 μg of recombinant DNA. At one day after transfection, foci of green fluorescent cells were visible which developed into plaques on the following days after infection (FIG. 3). From these results we concluded that the RacH strain of EHV-1 was cloned as an infectious full-length viral DNA in Escherichia coli. Deletion of gene 71 in RacH-BAC resulted in a less than 10% reduction in plaque size (FIG. 3).

TABLE 1

| Seq. ID No. | Primer | Sequence | Fragment or plasmid generated |
|---|---|---|---|
| 1. | Gen71 1.Fr. for | 5'-GCAggtaccTTTGCACAACTTTAGGATGAC-3' | 2.0-kb flank for p71-pHA2 |
| 2. | Gen71 1.Fr. rev | 5'-GATggatccCTttaattaaGTAGACGCGGCTGTAGTAAC-3' | 2.0-kb flank for p71-pHA2 |
| 3. | Gen71 2.Fr. for | 5'-ACAgtcgacCTttaattaaTCGGGGAACTACTCACACTC-3' | 2.4-kb flank for p71-pHA2 |
| 4. | Gen71 2.Fr. rev | 5'-CGAgcatgcAGTTTTACGCGAAGGATATAC-3' | 2.4-kb flank for p71-pHA2 |
| 5. | Kan950 for | 5'-GCCAGTGTTACAACCAATTAACC-3' | $Kan^r$950 gene |
| 6. | Kan950 rev | 5'-CGATTTATTCAACAAAGCCACG-3' | $Kan^r$950 gene |
| 7. | gM950EHV for | 5'-GGTTTCAAATTCCTCGCTCACCACGTCGTAAATTGGCTCT TCTGCGTCCGGCCAGTGTTACAACCAATTAAC-3' | $Kan^r$950 gene for gM deletion |
| 8. | gM950EHV rev | 5'-AAAACCACAGCGTGGTCGATGGAGTGTGGATGCGGCAG ATAGCTGGTGGACGATTTATTCAACAAAGCCACG-3' | $Kan^r$950 gene for gM deletion |
| 9. | gD-950 for | 5'-CGCCCACTCAACTTCCAACTTCGCTTTAGTGGCTGCGACC ACGCTAACAGCGATTTATTCAACAAAGCCACG-3' | $Kan^r$950 gene for gD deletion |
| 10. | gD-950-1 rev | 5'-TTCTTCCGACGCAAGCAGACGTATAGAATGACGCCCACC AATACTAGGCCAGTGTTACAACAAATTAACC-3' | $Kan^r$950 gene for gD deletion |

Mutagenesis of EHV-1 BACs

For mutagenesis of RacH-BAC DNA in *Escherichia coli*, recE- and recT-catalyzed reactions promoting homologous recombination between linear DNA fragments, also referred to as E/T cloning, was performed (Muyrers et al., 1999; Zhang et al., 1999). Plasmid pGETrec (kindly provided by Dr. Panos Ioannou, Murdoch Institute, Melbourne, Australia) harboring the recE, recT and bacteriophage λ gam gene (Narayanan et al., 1999) was transformed into RacH-BAC-containing DH10B cells. After induction of recE, recT and gam by addition of 0.2% arabinose, electrocompetent cells were prepared essentially as described (Muyrers et al., 1999). To delete the gD and gM gene in RACH-BAC, the kanamycin resistance gene ($kan^R$) of plasmid pACYC177 (Stratagene) was amplified by PCR. The designed primers contained 50 nucleotide homology arms bordering the desired deletion within gD or gM and 20 nucleotides for amplification of $kan^R$ (Table 1). The resulting 0.95 kbp fragment was purified from an agarose gel (Qiagen) and electroporated into pGETrec-containing RacH-BAC cells. Colonies harboring the $cam^R$ and $kan^R$ genes were identified on plates containing both antibiotics.

H-BACΔgD and H-BACΔgM DNA were isolated from *Escherichia coli* by chromatography and subjected to restriction enzyme digestion and Southern blot analysis (FIG. 4) transfection studies were performed. Whereas RacH-BAC and H-BACΔgM were able to induce viral plaques on RK13 cells, H-BACΔgD was able to induce plaques on cells expressing gD in trans only. The gD cells transiently expressed EHV-1 gD after transfection of a recombinant plasmid in which gD is under control of the HCMV immediate early promoter/enhancer. These observations indicated that EHV-1 gD is essential for virus growth in vitro.

REFERENCES

Adler H., M. Messerle, M. Wagner, and U. H. Koszinowski U H. 2000. Cloning and mutagenesis of the murine gammaherpesvirus 68 genome as an infectious bacterial artificial chromosome. J. Virol. 74: 6964-6974.

Borst, E. M., G. Hahn, U. H. Koszinowski, and M. Messerle. 1999. Cloning of the human cytomegalovirus (HCMV) genome as an infectious bacterial artificial chromosome in *Escherichia coli*: a new approach for construction of HCMV mutants. J. Virol. 73: 8320-8329

Flowers, C. C. and O'Callaghan, D. J., 1992. The equine herpesvirus type 1 (EHV-1) homolog of herpes simplex virus type 1 US9 and the nature of a major deletion within the unique short segment of the EHV-1 KyA strain genome. Virology 190, 307-315.

Hübert, P. H., Birkenmaier, S., Rziha, H. J. and Osterrieder, N., 1996. Alterations in the equine herpesvirus type-1 (EHV-1) strain RacH during attenuation. J. Vet. Med. B 43, 1-14.

Marshall K R, Sun Y, Brown S M, Field H J. An equine herpesvirus-1 gene 71 deletant is attenuated and elicits a protective immune response in mice. Virology. 1997 28; 231(1):20-7.

Mayr, A., Pette, J., Petzoldt, K. and Wagener, K., 1968. Untersuchungen zur Entwicklung eines Lebendimpfstoffes gegen die Rhinopneumonitis (Stutenabort) der Pferde. J. Vet. Med. B 15, 406-418.

Meindl, A. and Osterrieder, N., The equine herpesvirus 1 Us2 homolog encodes a nonessential membrane-associated virion component J. Virol., 73(4):3430-7, 1999.

Messerle, M., I. Crnkovic, W. Hammerschmidt, H. Ziegler, and U. H. Koszinowski. 1997. Cloning and mutagenesis of a herpesvirus genome as an infectious bacterial artificial chromosome. Proc. Natl. Acad. Sci. U.S.A. 94: 14759-14763.

Mumford, J. A., Hannant, D. A., Jessett, D. M., O'Neill, T., Smith, K. C. and Ostlund, E. N., 1995. Abortigenic and neurological disease caused by experimental infection with liquid herpesvirus-1. In "Proceedings $7^{th}$ International Conference of Equine Infectious Disease" (H. Nakajima and W. Plowright, Eds.) pp. 261-175. R&W Publ., Newmarket, U.K. United Kingdom.

Muyrers, J. P., Y. Zhang, G. Testa, and A. F. Stewart. 1999. Rapid modification of bacterial artificial chromosomes by ET-recombination. Nucleic Acids Res. 27: 1555-1557.

Narayanan, K., R. Williamson, Y. Zhang, A. F. Stewart, and P. A. Ioannou. 1999. Efficient and precise engineering of a 200 kb beta-globin human/bacterial artificial chromosome in *E. coli* DH10B using an inducible homologous recombination system. Gene Ther. 6: 442-447.

Neubauer, A., Beer, M., Brandmüller, C., Kaaden, O.-R. and Osterrieder, N., 1997. Equine herpesvirus 1 mutants devoid of glycoprotein B or M are apathohenic for mice but induce protection against challenge infection. Virology 239, 36-45.

Osterrieder, N., Neubauer, A., Brandmüller, C., Braun, B., Kaaden, O.-R. and Baines, J. D., 1996. The equine herpesvirus 1 glycoprotein gp21/22a, the herpes simplex virus type 1 gM homolog, is involved in virus penetration and cell-to-cell spread of virions. Journal of virology, June 1996, p. 4110-4115.

Osterrieder, N., Wagner, R., Brandmüller, C., Schmidt, P., Wolf, H. and Kaaden, O.-R., 1995. Protection against EHV-1 challenge infection in the murine model after vaccination with various formulations of recombinant glycoprotein gp14 (gB). Virology 208, 500-510.

Peeters, B., Biendowska-Szewcyk, K., Hulst, M., Giellens, A. and Kimman, T., 1997. Biologically safe, non-transmissible pseudorabies virus vector vaccine protects pigs against both Aujeszky's disease and classical swine fever. J. Gen. Virol. 78, 3311-3315.

Sambrook, J., Fritsch, D. F. and Maniatis, T., 1989. Molecular Cloning: A laboratory manual. $2^{nd}$ ed. Cold Spring Harbor Laboratory Press, Cold Spring Harbor, N.Y.

Sun Y, MacLean A R, Dargan D, Brown S M. Identification and characterization of the protein product of gene 71 in equine herpesvirus 1. J Gen Virol. 1994 November; 75 (Pt 11):3117-26.

Telford, E. A. R., Watson, M. S., McBride, K. and Davison, A. J., 1992. The DNA sequence of equine herpesvirus-1. Virology 189, 304-316.

Tewari, D., Whalley, J. M., Love, D. N. and Field, H. J., 1994. Characterisation of immune responses to baculovirus expressed equine herpesvirus type I glycoproteins D and H in a murine model. J. Gen. Virol. 75, 1735-1741.

Wagner, M., S. Jonjic, U. H. Koszinowski, and M. Messerle. 1999. Systematic excision of vector sequences from the BAC-cloned herpesvirus genome during virus reconstitution. J. Virol. 73:7056-7060.

Zhang, Y., F. Buchholz, J. P. Muyrers, and A. F. Stewart. 1998. A new logic for DNA engineering using recombination in *Escherichia coli*. Nature Genet. 20:123-128.

What is claimed is:

1. A bacterial artificial chromosome vector as deposited under ECACC accession No. 01032704.

2. The bacterial artificial chromosome vector according to claim 1, wherein said bacterial artificial chromosome vector as deposited under ECACC accession No. 01032704 further lacks a sequence coding for glycoprotein gM.

3. The bacterial artificial chromosome vector of claim 1, wherein a foreign sequence of another viral, bacterial or parasitic pathogen is added to said bacterial artificial chromosome vector as deposited under ECACC accession No. 01032704.

4. A polynucleotide encoding an artificial chromosome vector, which vector is characterized in that it comprises the entire genome of an EHV strain deposited under ECACC accession No. 01032704.

5. A method for generating EHV which comprises infecting a suitable cell line with the artificial chromosome vector according to claim 1, allowing the vector to replicate and shed virus, collecting the shed virus and purifying the collected virus.

6. A method for generating an attenuated EHV which comprises modifying by molecular biology techniques the EHV sequence contained in an artificial chromosome vector according to claim 1.

7. The method according to claim 1 wherein a foreign sequence of another viral, bacterial or parasitic pathogen is added to the artificial chromosome vector.

8. A method for generating a virulent EHV which comprises modifying by molecular biology techniques the EHV sequence contained in an artificial chromosome vector according to claim 1.

9. The method according to claim 8 wherein a foreign sequence of another viral, bacterial or parasitic pathogen is added to the artificial chromosome vector.

* * * * *

SEQUENCE LISTING

<160> NUMBER OF SEQ ID NOS: 10

<210> SEQ ID NO 1
<211> LENGTH: 30
<212> TYPE: DNA
<213> ORGANISM: Artificial Sequence
<220> FEATURE:
<223> OTHER INFORMATION: primer

<400> SEQUENCE: 1
gcaggtacct ttgcacaact ttaggatgac				30

<210> SEQ ID NO 2
<211> LENGTH: 39
<212> TYPE: DNA
<213> ORGANISM: Artificial Sequence
<220> FEATURE:
<223> OTHER INFORMATION: primer

<400> SEQUENCE: 2
gatggatccc tttaattaag tagacgcggc tgtagtaac			39

<210> SEQ ID NO 3
<211> LENGTH: 39
<212> TYPE: DNA
<213> ORGANISM: Artificial Sequence
<220> FEATURE:
<223> OTHER INFORMATION: primer

<400> SEQUENCE: 3
acagtcgacc tttaattaat cggggaacta ctcacactc			39

<210> SEQ ID NO 4
<211> LENGTH: 30
<212> TYPE: DNA
<213> ORGANISM: Artificial Sequence
<220> FEATURE:
<223> OTHER INFORMATION: primer

<400> SEQUENCE: 4
cgagcatgca gttttacgcg aaggatatac			30

<210> SEQ ID NO 5
<211> LENGTH: 23
<212> TYPE: DNA
<213> ORGANISM: Artificial Sequence
<220> FEATURE:
<223> OTHER INFORMATION: primer

<400> SEQUENCE: 5
gccagtgtta caaccaatta acc			23

<210> SEQ ID NO 6
<211> LENGTH: 22
<212> TYPE: DNA
<213> ORGANISM: Artificial Sequence
<220> FEATURE:
<223> OTHER INFORMATION: primer

<400> SEQUENCE: 6
cgatttattc aacaaagcca cg			22

<210> SEQ ID NO 7
<211> LENGTH: 72

-continued

```
<212> TYPE: DNA
<213> ORGANISM: Artificial Sequence
<220> FEATURE:
<223> OTHER INFORMATION: primer

<400> SEQUENCE: 7
ggtttcaaat tcctcgctca ccacgtcgta aattggctct tctgcgtccg gccagtgtta      60
caaccaatta ac                                                         72

<210> SEQ ID NO 8
<211> LENGTH: 72
<212> TYPE: DNA
<213> ORGANISM: Artificial Sequence
<220> FEATURE:
<223> OTHER INFORMATION: primer

<400> SEQUENCE: 8
aaaaccacag cgtggtcgat ggagtgtgga tgcggcagat agctggtgga cgatttattc      60
aacaaagcca cg                                                         72

<210> SEQ ID NO 9
<211> LENGTH: 72
<212> TYPE: DNA
<213> ORGANISM: Artificial Sequence
<220> FEATURE:
<223> OTHER INFORMATION: primer

<400> SEQUENCE: 9
cgcccactca acttccaact tcgctttagt ggctgcgacc acgctaacag cgatttattc      60
aacaaagcca cg                                                         72

<210> SEQ ID NO 10
<211> LENGTH: 70
<212> TYPE: DNA
<213> ORGANISM: Artificial Sequence
<220> FEATURE:
<223> OTHER INFORMATION: primer

<400> SEQUENCE: 10
ttcttccgac gcaagcagac gtatagaatg acgcccacca atactaggcc agtgttacaa      60
caaattaacc                                                            70
```